United States Patent [19]

Jensen et al.

[11] Patent Number: 5,460,823
[45] Date of Patent: Oct. 24, 1995

[54] PROCESS OF PREPARING A WATER DISPERSIBLE HYDROPHOBIC OR AEROPHILIC SOLID

[75] Inventors: Nina M. Jensen, Hellerup; Per Vilstrup, Copenhagen; Marianne Winning, Kokkedal, all of Denmark

[73] Assignee: Danochemo A/S, Ballerup, Denmark

[21] Appl. No.: 187,134

[22] Filed: Jan. 27, 1994

Related U.S. Application Data

[63] Continuation of Ser. No. 855,641, filed as PCT/DK9/00278, Nov. 2, 1990, abandoned.

[30] Foreign Application Priority Data

Nov. 2, 1989 [DK] Denmark ................................. 5462/89

[51] Int. Cl.$^6$ ......................................... A61K 9/48
[52] U.S. Cl. ........................ 424/451; 426/73; 426/78
[58] Field of Search ........................ 424/451; 426/540, 426/73; 252/311

[56] References Cited

U.S. PATENT DOCUMENTS

| | | | |
|---|---|---|---|
| 2,876,160 | 3/1959 | Schoch et al. | 167/82 |
| 3,110,598 | 11/1963 | Muller | 426/540 |
| 3,206,316 | 9/1965 | Klaul | 426/540 |
| 3,526,682 | 9/1970 | Timreck | 264/4 |
| 3,529,065 | 9/1970 | Flandreau, Jr. | 514/725 |
| 4,006,025 | 2/1977 | Swank et al. | 96/129 |
| 4,519,961 | 5/1985 | Schumacher et al. | 264/4.6 |
| 4,522,743 | 6/1985 | Horn et al. | 252/311 |
| 4,726,955 | 2/1988 | Horn et al. | 426/73 |

FOREIGN PATENT DOCUMENTS

| | | |
|---|---|---|
| 034771 | 8/1981 | European Pat. Off. . |
| 074050 | 8/1982 | European Pat. Off. . |
| 0333523 | 9/1989 | European Pat. Off. . |
| 1617737 | 7/1967 | Germany . |
| 2820981 | 4/1979 | Germany . |
| 420817 | 4/1960 | Switzerland . |
| 431252 | 4/1961 | Switzerland . |
| 2122085 | 1/1984 | United Kingdom . |

OTHER PUBLICATIONS

Verlag Paul Parey, "Toxikologisch–hygienische...", 1987, pp. 130 and 136–139.
Lee, Chen–Hsiung, "Synthesis and Characterization...", 1976, dissertation, pp. 9 and 113.
Walford (ed.), Development in Food Colours 1, 1980, pp. 68–69.
Merck Index, 10th edition, 1983, pp. 258–259.
Bauernfeind et al., "Coloring Fat–Base Foods with—Carotene" in *Food Technology*, 12 (1958) pp. 527–535.
Dialog Information Services, File 350: World Patent Index 1963–1980, WPI Acc. No. 78–4130A/26 & RD,A, 1700 64, 10 Jun. 1978 (Abstract).

Primary Examiner—Thurman K. Page
Assistant Examiner—William E. Benston, Jr.
Attorney, Agent, or Firm—Keil & Weinkauf

[57] ABSTRACT

A process for producing hydrophobic or aerophobic solids having a particle size not exceeding 10 μm, which solids can be dispersed in water in the form of discrete microparticles. In the process the solids are milled in an aqueous medium in the presence of a hydrocolloid to obtain a suspension containing suspended particles having an average particle size not exceeding 10 μm. The suspension is then finely divided and dried to form a powder.

18 Claims, No Drawings

PROCESS OF PREPARING A WATER DISPERSIBLE HYDROPHOBIC OR AEROPHILIC SOLID

This application is a continuation of application Ser. No. 855,641, filed as PCT/DK90/00278, Nov. 2, 1990, now abandoned.

BACKGROUND OF THE INVENTION

1. Field of the Invention

The present invention relates to a process of preparing a hydrophobic or aerophilic powdered solid which is dispersible in water or in an aqueous solution (in the following referred to as a water dispersible solid) in the form of discrete microparticles.

2. The Prior Art

More specifically the invention relates to a process of preparing water dispersible hydrophobic or aerophilic powdered colorants and biologically active solids.

It is well known that the coloring effect of a colorant or pigment dispersed in an aqueous medium, increases with decreasing particle size of the colorant or pigment and that the color intensity of the dispersion increases with increasing dispersability.

It is also well known that the bioavailability of biologically active powdered solids, such as carotenoids and drugs, such as griseofulvin, ibuprofen, benzodiazepines and hormones, such as progesteron dispersed in an aqueous medium increases with decreasing particle size of the dispersed solid.

Therefore, there is a need for providing water dispersible hydrophobic or aerophilic solids of a small particle size, e.g., a particle size not exceeding 10 μm, and more preferably not exceeding 2 μm.

Various methods of reducing the particle size of hydrophobic/aerophilic compounds to a maximum average of 10 μm have been disclosed. It is known to mill β-carotene together with edible oil in a colloid mill (Chimia 21, 329 (67)). Using this method it is possible to achieve a β-carotene content in the oil of about 30%.

Published Japanese patent application No. 57-3861 discloses a process for preparation of a water-dispersible carotenoid formulation which comprises mixing and grinding a carotenoid with gum arabic in a dry state using a grinding apparatus, such as rotary ball mills, vibration ball mills, and hammer mills. Following grinding the solid product can be dissolved in water and the resulting solution can be converted into a powder by spray drying or freeze drying. A powder formulation having a carotenoid content of 1.5 percent by weight is obtained. A disadvantage of this method is that the milled compounds may be damaged due to the increase of temperature during grinding or milling in the dry state because of the lack of efficient cooling equipment. Furthermore, it is difficult to prevent oxidation of the milled compounds during a dry grinding or milling operation.

Moreover, Chimia 21,329 (1967), DE application No. 12 11 911 and DE publication No. 25 34 091 disclose methods of dissolving the active compound in a chlorinated organic solvent, emulsifying the solution in a gelatine/sucrose solution and extracting the solvent from the emulsion causing the active compound to crystallize in microcrystalline form. A disadvantage of this method is that it is technically impossible to remove the organic solvent completely and the solvent is a potential hazard during the process and as residues in the final product.

DK-B-154.395 discloses a preparation, which has been prepared by dissolving a carotenoid or a retinoid in an organic solvent that is miscible with water at a temperature of between 50° and 200° C. optionally under pressure in less than 10 sec. The resulting molecular-disperse solution is immediately mixed with an aqueous solution of a hydrocolloid, followed by an isolation of the colloid-disperse particles from the solvent to obtain a dry free flowing powder that can be dispersed in water. This method is disadvantageous because of the use of organic solvents that require special equipment for collection of the solvents. Furthermore, the concentration of the active compound will be relatively low in the final product, i.e., a maximum of about 20 percent by weight. Furthermore, it is stated that it has not been possible to mill hydrophobic solids, such as β-carotene in water or in an aqueous system to obtain the desired particle size without damage to the active compounds.

Research Disclosure (RD) 17064, June 1978, describes a method of preparing stable carotenoid colorants, wherein the carotenoids are milled in ball mills in an aqueous or oily medium in the presence of a protective colloid and a carrier, such as gelatine, and an ionic emulgator. The milling in the aqueous medium is followed by a spray drying process resulting in a water dispersible colorant having a carotenoid content of about 10%. However, the ionic emulgator will be present in the final product, which is undesirable especially when the colorant is to be used in food products.

It is well known that an aqueous dispersion of particles of hydrophobic/aerophilic solids can be prepared by mixing a hydrophobic/aerophilic solid with water in the presence of a wetting agent or tenside, such as lauryl sulfate or polysorbate. Without the use of a wetting agent milling is impossible, and without sufficient wetting the particles will agglomerate and the suspension will become too viscous for milling.

SUMMARY OF THE INVENTION

The object of the invention is to provide a process for preparing a hydrophobic/aerophilic solid that can be dispersed in water in the form of discrete microparticles without the use of oils, organic solvents and/or wetting agents or similar additives to form a microencapsulated product having a concentration of up to 71% of hydrophobic/aerophilic solid.

This object can be achieved by the process of the invention which process is characterized in that the solid is milled in an aqueous medium in the presence of a hydrocolloid in an amount of not less than about 10 percent by weight of the hydrophobic/aerophilic solid, to obtain a suspension containing suspended particles of an average particle size not exceeding 10 μm, and finely dividing and drying the suspension thus formed to obtain a powder.

It is further assumed that the hydrocolloid, such as gelatine, provides sufficient wetting of the hydrophobic/aerophilic material to avoid agglomeration of the fine particles formed during the milling process. The required minimum amount of the hydrocolloid to provide sufficient wetting of the solid is dependent on the specific solid and hydrocolloid and the presence of other excipients.

It is assumed that the hydrocolloid protects the new surfaces resulting from the milling of the relatively coarse particles of the hydrophobic/aerophilic material by creating a thin film that is intimately bound to the reactive new surfaces, thus preventing the particles to agglomerate due to hydrophobic interactions. Furthermore, the hydrocolloid reduces the surface tension and increases the dispersability of the final product.

Moreover, the hydrocolloid protects the milled particles in both the liquid and the dried state, thus preventing recrystallisation and crystal growth of materials, such as low melting hormones, low melting lipids and other fat soluble materials.

Surprisingly, it has been found that by using the process of the invention microencapsulated products having a concentration of hydrophobic/aerophilic solid of up to 71% can be obtained.

The milling is preferably effected in a bead mill or any similar mill having cooling equipment for maintaining the temperature below a value at which the hydrofobic/aerophilic materials are decomposed and wherein the materials can be kept under a controlled atmosphere.

In a preferred embodiment of the process according to the invention the hydrophobic/aerophilic solid is preferably added to an aqueous solution of a hydrocolloid that has been degassed by boiling under vacuum and preferably covered by $N_2$ or any other inert gas. The mixture is then stirred at a temperature of between 0° C. and 100° C., the lower limit being determined by the temperature at which the hydrocolloid forms a gel and the upper limit being determined by the heat lability of the active compound. Antioxidants may be added to the suspension.

The suspension is transferred to the mill which can be any type that is capable of milling the solid to a maximum particle size of 10 μm, is equipped with a cooling jacket and wherein the atmosphere can be controlled. During the milling the temperature is between 0° C. and 100° C., preferably above 60° C. and the pressure is preferably between 0 and 5 bar. The suspension may be pumped through the mill in a peristaltic pump or using a gear pump having a flow of from 50 to 1000 ml/min, preferably from 150 to 400 ml/min.

Solid hydrophobic/aerophilic materials that can be milled and encapsulated in the process according to the invention include carotenoids, such as β-carotene, annatto, bixin, norbixin, capsanthin, capsorubin, lycopene, β-apo-8'-carotenal, flavoxanthin, lutein, cryptoxanthin, rubixanthin, violaxanthin, rhodoxanthin, canthaxanthin, astaxanthin and citranaxanthin and derivatives thereof; natural colorants, such as curcumin, chlorophyll, carmine, etc.; and drugs, such as griseofulvin, ibuprofen, benzodiazepines, phenacetin and hormones.

Hydrocolloids that can be used in the process according to the invention include exudates, such as gum arabic, tragacanth, gum karaya, gum ghatti; extracts from seaweed, such as agar, alginate, carrageenan and furcellaran; extracts from plants, such as pectin and arabinogalactan; extracts from marine and terrestrial animals, such as gelatines and other proteinaceous hydrocolloids; flours from seeds, such as guar, locust bean, soya bean; proteins from seeds, such as soya bean protein; flours from cereals, such as starches and microcrystalline cellulose; biosynthetic or fermentation derived hydrocolloids, such as dextran, xanthan and curdlan; chemically modified hydrocolloids, such as cellulose derivatives, including methyl cellulose, and other derivatives, including modified starches and low methoxyl pectin; synthetic hydrocolloids, such as polyvinylpyrrolidon, carboxyvinyl polymers, etc.

The aqueous medium can optionally further contain excipients in an amount of up to 70 percent by weight of the suspension, such as a dissolved carbohydrate, such as sorbitol and sucrose, and/or an antioxidant or an oil containing an antioxidant.

The resulting suspension is finely divided and dried using any combination of conventional methods, such as spray cooling, spray drying, modified spray drying or sheet drying and crushing, etc.

Another advantage of the process according to the invention is that the hydrocolloid used in the milling of a hydrophobic/aerophilic solid can act as a matrix material in a subsequent encapsulation process. Such processes will be described in the following.

SPRAY COOLING

In a spray cooling process a suspension containing a hydrocolloid is preferably sprayed using an atomizing nozzle or an atomizing wheel at a temperature higher than the gelling/melting point, i.e. from about 38° to about 95° C. and at a viscosity of preferably between 50 and 300 mPa.s in a spraying chamber, wherein the temperature is from 0° to about 40° C., thereby forming microcapsules of gelatinized hydrocolloid.

A powdery spraying excipient is preferably blown into the spraying chamber in order to prevent agglomeration of the gelatinized microcapsules and to prevent adherence to the chamber wall. The spraying excipient is preferably supplied in an amount of from 5 to 50 percent by weight based on the weight of the final product.

The microcapsules are transferred a fluidized bed, wherein they may be dried to a residual water content of between 0 and 10% (preferably from 2 to 5%) and in which excessive spraying excipient is separated. The drying air temperature is preferably from about 0° to about 60° C.

MODIFIED SPRAY DRYING

The modified spray drying process differs from the spray cooling process in that the temperature in the spraying chamber is high, preferably between 50° and 95° C.

In the modified spray drying process the suspension is preferably sprayed at a temperature of from 5° to 99° C. and at a viscosity of from 50 to 300 mPa.s using an atomizing nozzle or an atomizing wheel in a spraying chamber, wherein the temperature is from 50° to 95° C.

A powdery spraying excipient may be blown into the spraying chamber in order to prevent agglomeration of the formed microcapsules and to prevent adherence to the chamber wall. The spraying excipient is preferably supplied in an amount of from 5 to 50 percent by weight based on the weight of the final product.

The powdered microcapsules may be transferred to a fluidized bed, wherein they may be dried to a residual water content of between 0 and 10% (preferably from 2 to 5%) and excessive spraying excipient is separated. The drying air temperature is preferable from about 0° to about 60° C.

In the spray cooling, spray drying and modified spray drying processes the following spraying excipients may be used: starches, modified starches, tricalcium phosphate, lactose, mannitol, ethyl cellulose, coagulated albumin, hardened gelatine, casein, stearat-Ca, stearat-Na, metal soaps, hydrogenated ricinus oil, polyoxide, talcum, waxes, and silicates.

In a sheet drying process the suspension is preferably dried in a thin layer to form a solidified suspension which subsequently may be ground into a powder. Alternatively, the suspension may be emulsified in an oil, washed and dried/spray dried or extruded, drum dried and crushed or treated by any combination of known methods of finely dividing and drying or drying and finely dividing.

Microencapsulated β-carotene may be a constituent of vitamin tablets. However, because of the relatively low concentration of β-carotene in microcapsules prepared using the known techniques, it is necessary to formulate the vitamin tablets with a relatively large amount of β-carotene microcapsules resulting in bulky tablets. This obstacle is overcome when tablets are formulated with microcapsules having a high β-carotene content that are prepared according to the invention.

Another advantage of the hydrocolloid protection of microparticles of hydrophobic/aerophilic compounds, such as phenacetin, is an improved performance when preparing tablets from such compounds.

It is preferred to include an antioxidant in the suspension when the active compound is sensitive to oxygen. The antioxidant can be water soluble or water insoluble and can be incorporated during the milling process or in a subsequent emulsification process.

The dispersability of the microencapsulated product is evaluated visually after the addition of 0.2 g of microencapsulated product to 200 ml of water having a temperature of 40°–45° C. in a beaker. The dispersability is satisfactory when the microencapsulated particles are immediately wetted and a uniform dispersion is formed after 2 minutes of stirring. When viewed in a light microscope in transparency the dispersion consists of predominantly discrete particles.

In the microencapsulated product prepared according to the above process containing a hydrophobic/aerophilic solic having a maximum average particle size not exceeding 10 μm and which can be dispersed in water in the form of discrete microparticles, the amount of hydrophobic/aerophilic solid is up to 71 percent by weight of the microencapsulated product. The microcapsules prepared by the process described above can be used in pharmaceutical compositions, feeds and foodstuffs.

EXAMPLE 1

1000 g of β-carotene was added in a $N_2$-atmosphere to a solution of 584 g of 240 Bloom gelatine and 100 g of Na-ascorbat in 2800 g of water having a temperature of 65° C. Before the addition of β-carotene the solution had been degassed using a vacuum and the pressure had been brought to equilibrium with $N_2$. When the β-carotene crystals were sufficiently wetted, the suspension was milled in a bead mill, DynoMill type KDL, during 1 hour of recirculation. The milled suspension was transferred in a $N_2$-atmosphere to a degassed aqueous solution of 1300 g of gelatine and 2044 g of sucrose, wherein 9.5 g of ascorbyl palmitate and 14.3 g of a mixture of α-, β-, and γ-tocopherol had been emulsified. After being thoroughly mixed the resulting suspension was spray cooled in a conventional manner.

The following intervals of product characteristics for four products were obtained:

| | |
|---|---|
| β-carotene content: | 13.2–13.8 percent by weight |
| extractable β-carotene: | 0.3–0.8 percent by weight |
| absorption ratio $A_{452\ nm}:A_{483\ nm}$: | 1.16 |
| absorption ratio $A_{452\ nm}:A_{340\ nm}$: | 14.7–15.2 |
| stability after 6 months at 22° C.: | 100% of original β-carotene content |

The visual dispersability test was satisfactory.

EXAMPLE 2

600 g of β-carotene was added in a $N_2$-atmosphere to a solution of 350 g of 240 Bloom gelatine and 60 g of Na-ascorbat in 1500 g of water having a temperature of 65° C. Before the addition of β-carotene the solution had been degassed using a vacuum and the pressure had been brought to equilibrium with $N_2$. When the β-carotene crystals were sufficiently wetted, the suspension was milled in a bead mill, DynoMill type KDL, during 1 hour of recirculation. The milled suspension was transferred to a degassed aqueous solution of 184 g of gelatine and 484 g of sucrose in a $N_2$-atmosphere, wherein 7.9 g of a mixture of α-, β-, and γ-tocopherol had been emulsified. After being thoroughly mixed the resulting suspension was spray cooled in a conventional manner.

The following product characteristics were obtained:

| | |
|---|---|
| β-carotene content: | 16.9 percent by weight |
| extractable β-carotene: | 0.4 percent by weight |
| absorption ratio $A_{452\ nm}:A_{483\ nm}$: | 1.16 |
| absorption ratio $A_{452\ nm}:A_{340\ nm}$: | 15.4 |
| stability after 3 months at 22° C.: | 98.7% of original β-carotene content |

The visual dispersability test was satisfactory.

EXAMPLE 3

500 g of β-carotene was added to a solution of 146 g of 240 Bloom gelatine and 50 g of Na-ascorbat in 1000 g of water having a temperature of 65° C. When the β-carotene crystals were sufficiently wetted, the suspension was milled in a bead mill, DynoMill type KDL, during 1 hour of recirculation. In the milled suspension 7.1 g of a mixture of α-, β-, and γ-tocopherol had been emulsified. After being thoroughly mixed the resulting suspension was spray cooled in a conventional manner.

The following product characteristics were obtained:

| | |
|---|---|
| β-carotene content: | 42.5 percent by weight |
| absorption ratio $A_{452\ nm}:A_{483\ nm}$: | 1.19 |
| absorption ratio $A_{452\ nm}:A_{340\ nm}$: | 10.3 |

The visual dispersability test was satisfactory.

EXAMPLE 4

360 g of β-carotene was added to a solution of 210 g of low Bloom gelatine and 36 g of Na-ascorbat in 935 g of water having a temperature of 65° C. When the β-carotene crystals were sufficiently wetted, the suspension was milled in a bead mill, DynoMill type KDL, during 1 hour of recirculation. The milled suspension was transferred to an aqueous solution of 648 g of high Bloom gelatine and 556 g of sucrose, wherein a mixture of 151 g of coconut oil and 0.9 g of a mixture of α-, β-, and γ-tocopherol had been emulsified. After being thoroughly mixed the resulting suspension was spray cooled in a conventional manner.

The following product characteristics were obtained:

| | |
|---|---|
| β-carotene content: | 11.3 percent by weight |
| extractable β-carotene: | 0.1 percent by weight |
| absorption ratio $A_{452\ nm}:A_{483\ nm}$: | 1.16 |
| absorption ratio $A_{452\ nm}:A_{340\ nm}$: | 14.8 |
| stability after 3 months at 22° C.: | 96.5% of original β-carotene content |

The visual dispersability test was satisfactory.

EXAMPLE 5

600 g of β-carotene was added in a $N_2$-atmosphere to a solution of 350 g of 70 Bloom gelatine and 60 g of Na-ascorbat in 1500 g of water having a temperature of 65° C. Before the addition of β-carotene the solution had been degassed using a vacuum and the pressure had been brought to equilibrium with $N_2$. When the β-carotene crystals were sufficiently wetted, the suspension was milled in a bead mill, DynoMill type KDL, during 1 hour of recirculation. The milled suspension was transferred to a degassed aqueous solution of 592 g of 30 Bloom gelatine and 558 g of sucrose in a $N_2$-atmosphere, wherein a mixture of 117 g of coconut oil and 0.7 g of a mixture of α-, β-, and γ-tocopherol had been emulsified. After being thoroughly mixed the resulting suspension was subjected to a modified spray drying.

The following product characteristics were obtained:

| | |
|---|---|
| β-carotene content: | 11.4 percent by weight |
| extractable β-carotene: | 0.7 percent by weight |
| absorption ratio $A_{452\ nm}:A_{483\ nm}$: | 1.16 |
| absorption ratio $A_{452\ nm}:A_{340\ nm}$: | 14.4 |
| stability after 3 months at 22° C.: | 95.1% of original β-carotene content |

The visual dispersability test was satisfactory.

EXAMPLE 6

25 g of Canthaxanthin was added to a solution of 14.5 g of 106 Bloom gelatine and 2.5 g of Na-ascorbat in 70 g of water having a temperature of 65° C. When the cantaxanthin crystals were sufficiently wetted, the suspension was milled in a bead mill, DynoMill type KDL, during 1 hour. The milled suspension was transferred to an aqueous solution of 153 g of 240 Bloom gelatine and 153 g of sucrose, wherein 0.5 g of ascorbyl palmitate and 2.0 g of BHT and 10.0 g of ethoxyquin had been emulsified. After being thoroughly mixed the resulting suspension was spray cooled in a conventional manner.

The final product contained 4.4 percent by weight of canthaxanthin.

The visual dispersability test was satisfactory.

EXAMPLE 7

25 g of Astaxanthin was added to a solution of 14.5 g of 106 Bloom gelatine and 2.5 g of Na-ascorbat in 1500 g of water having a temperature of 65° C. When the astaxanthin crystals were sufficiently wetted, the suspension was milled in a bead mill, DynoMill type KDL, during 1 hour. The milled suspension was transferred to an aqueous solution of 153 g of 240 Bloom gelatine and 153 g of sucrose, wherein 0.5 g of ascorbyl palmitate and 2.0 g of BHT and 10.0 g of ethoxyquin had been emulsified. After being thoroughly mixed the resulting suspension was spray cooled in a conventional manner.

The final product contained 4.5 percent by weight of astaxanthin.

The visual dispersability test was satisfactory.

EXAMPLE 8

500 g of β-carotene was added to a solution of 250 g of gum arabic and 50 g of Na-ascorbat in 1750 g of water having a temperature of 65° C. When the β-carotene crystals were sufficiently wetted, the suspension was milled in a bead mill, DynoMill type KDL, during 1 hour of recirculation. The milled suspension was transferred to an aqueous solution of 916 g of gum arabic and 780 g of sucrose, wherein 7.4 g of a mixture of α-, β-, and γ-tocopherol had been emulsified. After being thoroughly mixed the resulting suspension was spray cooled in a conventional manner.

The following product characteristics were obtained:

| | |
|---|---|
| β-carotene content: | 8.9 percent by weight |
| absorption ratio $A_{452\ nm}:A_{483\ nm}$: | 1.16 |
| absorption ratio $A_{452\ nm}:A_{340\ nm}$: | 14.2 |

The visual dispersability test was satisfactory.

EXAMPLE 9

500 g of β-carotene was added to a solution of 200 g of Methocel® E5 and 50 g of Na-ascorbat in 2000 g of water having a temperature of 65° C. When the β-carotene crystals were sufficiently wetted, the suspension was milled in a bead mill, DynoMill type KDL, during 1 hour of recirculation. The milled suspension was transferred to an aqueous solution of 323 g of Methocel® E5 and 1224 g of sucrose, wherein 7.6 g of a mixture of α-, β-, and γ-tocopherol had been emulsified. After being thoroughly mixed the resulting suspension was subjected to a modified spray drying process in a conventional manner.

The following product characteristics were obtained:

| | |
|---|---|
| β-carotene content: | 4.0 percent by weight |
| absorption ratio $A_{452\ nm}:A_{483\ nm}$: | 1.19 |
| absorption ratio $A_{452\ nm}:A_{340\ nm}$: | 10.0 |

The visual dispersability test was satisfactory.

EXAMPLE 10

500 g of β-carotene was added to a solution of 500 g of Capsul® 50 g and of Na-ascorbat in 1500 g of water having a temperature of 65° C. When the β-carotene crystals were sufficiently wetted, the suspension was milled in a bead mill, DynoMill type KDL, during 1 hour of recirculation. The milled suspension was transferred to an aqueous solution of 665 g of Capsul® and 777 g of sucrose, wherein 7.2 g of a mixture of α-, β-, and γ-tocopherol had been emulsified. After being thoroughly mixed the resulting suspension was subjected to a modified spray drying process in a conventional manner.

The following product characteristics were obtained:

| | |
|---|---|
| β-carotene content: | 9.9 percent by weight |
| absorption ratio $A_{452\ nm}:A_{483\ nm}$: | 1.16 |
| absorption ratio $A_{452\ nm}:A_{340\ nm}$: | 13.6 |

The visual dispersability test was satisfactory.

EXAMPLE 11

500 g of β-carotene was added to a solution of 292 g of 240 Bloom gelatine in 1400 g of water having a temperature of 65° C. When the β-carotene crystals were sufficiently wetted, the suspension was milled in a bead mill, DynoMill type KDL, during 1 hour of recirculation. The milled suspension was transferred to an aqueous solution of 1132 g of 240 Bloom gelatine and 1298 g of sucrose, wherein 7.4 g of a mixture of α-, β-, and γ-tocopherol had been emulsified. After being thoroughly mixed the resulting suspension was spray cooled in a conventional manner.

The following product characteristics were obtained:

| | |
|---|---|
| β-carotene content: | 10.5 percent by weight |
| extractable β-carotene: | 0.3 percent by weight |
| absorption ratio $A_{452\ nm}:A_{483\ nm}$: | 1.17 |
| absorption ratio $A_{452\ nm}:A_{340\ nm}$: | 14.6 |

The visual dispersability test was satisfactory.

EXAMPLE 12

250 g of Ibuprofen was added to a solution of 146 g of 240 Bloom gelatine in 700 g of water having a temperature of 65° C. When the ibuprofen crystals were sufficiently wetted, the suspension was milled in a bead mill, DynoMill type KDL, during 1 hour of recirculation. The milled suspension was transferred to an aqueous solution of 566 g of 240 Bloom gelatine and 649 g of sucrose. After being thoroughly mixed the resulting suspension was spray cooled in a conventional manner.

The final product contained 12.9 percent by weight of ibuprofen.

EXAMPLE 13

300 g of Curcumin crystals was added to a solution of 300 g of low bloom gelatine and 300 g of sucrose in 900 g of water having a temperature of 65° C. When the curcumine crystals were sufficiently wetted, the suspension was milled in a bead mill, DynoMill type KDL, during 1 hour of recirculation. The milled suspension was transferred to a solution of 750 g of sucrose in 300 g of water. After being thoroughly mixed the resulting suspension was subjected to a modified spray drying process.

The final product contained 26.0 percent by weight of curcumin.

We claim:

1. A process of preparing a hydrophobic solid powder which is a carotenoid or a natural colorant and which can be dispersed in water in the form of discrete microparticles, comprising the steps of:
   a) providing a hydrophobic solid,
   b) adding the solid to an aqueous solution of a hydrocolloid comprising not less than about 10 percent by weight of said solid to obtain a mixture, which hydrocolloid is gelatine, gum arabic, soy bean protein or modified starch or mixtures thereof,
   c) stirring the mixture at a temperature between 0° C. and 100° C. to form a first aqueous suspension,
   d) transferring the first aqueous suspension to a mill having cooling equipment for maintaining the temperature below the decomposition temperature of said solid,
   e) wet grinding said solid which is present in said aqueous suspension in said mill at a temperature between 0° C. and 100° C. to obtain a second aqueous suspension wherein the maximum particle size of the solid is 10 μm, and
   f) finely dividing and drying said second aqueous suspension to obtain a powder.

2. A process according to claim 1, wherein the suspension containing suspended particles is finely divided and dried by spray cooling, conventional spray drying or modified spray drying.

3. A process according to claim 2, wherein the suspension containing suspended particles is finely divided and dried by spray cooling, conventional spray drying or modified spray drying.

4. A process according to claim 1, wherein the carotenoid is β-carotene, β-apo-8'-carotenal, canthaxanthin, and/or astaxanthin.

5. A process according to claim 1, wherein the natural colorant is curcumin.

6. A process according to claim 1, wherein the suspension contains a carbohydrate, in an amount of up to 70 percent by weight of the suspension.

7. A process according to claim 6, wherein the carbohydrate is sucrose.

8. A process according to claim 1, wherein the suspension further contains an antioxidant.

9. A process according to claim 1, wherein the hydrophobic solid is used in an amount which is sufficient to provide a microencapsulated product having a concentration of up to 71 percent by weight of hydrophobic solid.

10. A process of preparing an aerophilic solid powder which is a carotenoid or a natural colorant and which can be dispersed in water in the form of discrete microparticles, comprising the steps of:
    a) providing an aerophilic solid,
    b) adding the solid to an aqueous solution of a hydrocolloid comprising not less than about 10 percent by weight of said solid to obtain a mixture, which hydrocolloid is gelatine, gum arabic, soy bean protein or modified starch or mixtures thereof,
    c) stirring the mixture at a temperature between 0° C. and 100° C. to form a first aqueous suspension,
    d) transferring the first aqueous suspension to a mill having cooling equipment for maintaining the temperature below the decomposition temperature of said solid,
    e) wet grinding said solid which is present in said aqueous suspension in said mill at a temperature between 0° C. and 100° C. to obtain a second aqueous suspension wherein the maximum particle size of the solid is 10 μm, and
    f) finely dividing and drying said second aqueous suspension to obtain a powder.

11. A process according to claim 10, wherein the suspension containing suspended particles is finely divided and dried by spray cooling or spray drying.

12. A process according to claim 1, wherein the suspension containing suspended particles is finely divided and dried by spray cooling or spray drying.

13. A process according to claim 11, wherein the carotenoid is β-carotene, β-apo-8'-carotenal, canthaxanthin, and/or astaxanthin.

14. A process according to claim 11, wherein the natural colorant is curcumin, chlorophyll and/or carmine.

15. A process according to claim 11, wherein the suspension contains a carbohydrate in an amount of up to 70 percent by weight of the suspension.

16. A process according to claim 15, wherein the carbohydrate is sucrose.

17. A process according to claim 11, wherein the suspension further contains an antioxidant.

18. A process according to claim 11, wherein the aerophilic solid is used in an amount which is sufficient to provide a microencapsulated product having a concentration of up to 71 percent by weight of aerophilic solid.

* * * * *

UNITED STATES PATENT AND TRADEMARK OFFICE
CERTIFICATE OF CORRECTION

PATENT NO.: 5,460,823

DATED: October 24, 1995

INVENTOR(S): JENSEN et al.

It is certified that error appears in the above-identified patent and that said Letters Patent is hereby corrected as shown below:

Abstract:

On the title page, item [57], line 1, "aerophobic" should be --aerophilic--.

Column 10, claim 12, line 1, "claim 1" should be --claim 11--.

Signed and Sealed this

Second Day of July, 1996

*Attest:*

*Attesting Officer*

BRUCE LEHMAN

Commissioner of Patents and Trademarks